United States Patent
Kuwahara et al.

(10) Patent No.: US 9,881,518 B2
(45) Date of Patent: Jan. 30, 2018

(54) FOOD INTAKE CONTROLLING DEVICES AND METHODS

(71) Applicant: Empire Technology Development LLC, Wilmington, DE (US)

(72) Inventors: Noriaki Kuwahara, Nara (JP); Tsutomu Miyasato, Nara (JP); Rieko Kadobayashi, Kizugawa (JP); Koichi Nakayama, Saga (JP); Noriaki Mitsunaga, Yao (JP)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 232 days.

(21) Appl. No.: 14/547,703

(22) Filed: Nov. 19, 2014

(65) Prior Publication Data
US 2016/0140869 A1    May 19, 2016

(51) Int. Cl.
*G09B 19/00* (2006.01)
*G09B 5/00* (2006.01)
(Continued)

(52) U.S. Cl.
CPC ..... *G09B 19/0092* (2013.01); *G06F 19/3475* (2013.01); *G09B 5/00* (2013.01);
(Continued)

(58) Field of Classification Search
CPC .......... G06F 19/3475; G06F 19/3481; G06F 19/3406; G09B 19/0092; G09B 5/00;
(Continued)

(56) References Cited

U.S. PATENT DOCUMENTS

| 5,454,721 A * | 10/1995 | Kuch ............... G06F 19/3475 434/127 |
| 8,690,578 B1 * | 4/2014 | Nusbaum ............ G09B 19/00 128/905 |

(Continued)

FOREIGN PATENT DOCUMENTS

| WO | 2011163131 A2 | 12/2011 |
| WO | 20140160298 A1 | 10/2014 |

OTHER PUBLICATIONS

"COOKPAD," accessed at http://web.archive.org/web/20140715181828/http://cookpad.com/, accessed on Jul. 16, 2014, pp. 1-6.
(Continued)

*Primary Examiner* — Jack Yip
(74) *Attorney, Agent, or Firm* — Brundidge & Stanger, P.C.

(57) ABSTRACT

Technologies are generally described for controlling food intake. Example devices/systems described herein may include an image sensor, a dietary information identifier, a dietary management unit, and an image display unit. The image sensor may capture an image of a dish or a menu. The dietary information identifier may identify the dish or menu from the image and provide meal dietary information based on the identified dish or menu. The dietary management unit may store personal dietary information and determine combined dietary information based on the personal dietary information and the meal dietary information. The image display unit may process the captured image based on the combined dietary information in such a manner that a part of the captured image is hidden on an image display unit or a part of color or text information of the captured image is changed on the image display unit.

18 Claims, 6 Drawing Sheets

(51) Int. Cl.
  *G06F 19/00* (2011.01)
  *G06Q 50/12* (2012.01)
  *G01N 33/02* (2006.01)
  *A61B 5/00* (2006.01)
  *A61B 5/11* (2006.01)

(52) U.S. Cl.
  CPC ........... *A61B 5/0022* (2013.01); *A61B 5/1118* (2013.01); *G01N 33/02* (2013.01); *G06F 19/3481* (2013.01); *G06K 2209/17* (2013.01); *G06Q 50/12* (2013.01)

(58) Field of Classification Search
  CPC .... A61B 5/1118; A61B 5/0022; G06Q 50/12; G06K 2209/17; G01N 33/02
  USPC .............. 434/127; 600/301; 382/110; 705/15
  See application file for complete search history.

(56) References Cited

U.S. PATENT DOCUMENTS

| | | | |
|---|---|---|---|
| 2002/0027164 A1 | 3/2002 | Mault et al. | |
| 2002/0047867 A1 | 4/2002 | Mault et al. | |
| 2004/0023189 A1* | 2/2004 | Bateman | G09B 19/0092 434/127 |
| 2005/0171800 A1 | 8/2005 | Yamaguchi | |
| 2009/0012433 A1* | 1/2009 | Fernstrom | A61B 5/1112 600/593 |
| 2011/0243392 A1 | 10/2011 | Miyahara et al. | |
| 2012/0214140 A1 | 8/2012 | Brynelsen et al. | |
| 2013/0085345 A1* | 4/2013 | Geisner | G06Q 30/00 600/300 |
| 2013/0211814 A1 | 8/2013 | Derks et al. | |
| 2013/0300636 A1 | 11/2013 | Cunningham et al. | |
| 2014/0147829 A1* | 5/2014 | Jerauld | G06F 1/163 434/430 |
| 2014/0315161 A1* | 10/2014 | Sako | G09B 19/0092 434/127 |
| 2015/0071757 A1* | 3/2015 | Daczko | F16M 11/18 414/800 |
| 2015/0168365 A1* | 6/2015 | Connor | G01N 33/02 356/51 |
| 2016/0012749 A1* | 1/2016 | Connor | G09B 5/00 600/13 |
| 2016/0063734 A1* | 3/2016 | Divakaran | G06K 9/6202 382/110 |

OTHER PUBLICATIONS

"For monitor recruitment experience of "Health Promotion assist service"," NTT Communication Corporation, accessed at http://web.archive.org/web/20140329073654/http://www.ntt.com/release/monthNEWS/detail/20110217.html, Feb. 17, 2011, pp. 1-4.

"The development of the feeling of fullness "diet glasses" show me the big food," Livedoor, accessed at http://web.archive.org/web/20120514053510/http://news.livedoor.com/article/detail/6492103/, Apr. 22, 2012, pp. 1-4.

Slabodkin, G., "Google Glass could have strong potential for healthcare use," Fierce Mobile Health Care, accessed at http://www.fiercemobilehealthcare.com/story/google-glasses-could-have-strong-potential-healthcare-use/2013-03-18, Mar. 18, 2013, pp. 1-4.

Surti, S., "Google Glass App#8 : Nutrition facts," accessed at http://www.seebernetic.com/google-glass-app8-nutirition-facts/, Mar. 11, 2013, p. 1.

International Search Report and Written Opinion for International Patent Application No. PCT/US20151060859 dated Jan. 29, 2016, pp. 6.

* cited by examiner

FOOD INTAKE CONTROLLING DEVICES AND METHODS

BACKGROUND

Unless otherwise indicated herein, the approaches described in this section are not prior art to the claims in this application and are not admitted to be prior art by inclusion in this section.

Various systems have been proposed for assisting people in controlling the amount of food intake or keeping to a prescribed diet. For example, some systems advise a use to eat foods that are appropriate for keeping healthy condition of the user or not eat foods that are prohibited for managing diabetes, blood pressure, etc. Another example may be systems that require a user to manually input or detect various data such as the amount of food intake or exercise that the user has engaged in throughout the day. To assist the user to detect such data, various wearable devices such as a smart watch have been employed in cooperation with main controlling devices such as smartphones or tablet computers.

The above systems, however, have a variety of limitations. In particular, the advice that such systems provide may not be tailored sufficiently to the personal requirements of the user and/or often may not reflect current information about the user. Also, such systems may not provide measures that efficiently motivate the user to control the food intake or exercise based on his/her current health condition.

SUMMARY

Technologies generally described herein relate to controlling food intake.

Various example devices described herein may include one or more of an image sensor, a dietary information identifier, a dietary management unit, and/or an image display unit. The image sensor may be configured to capture an image of at least one of a dish or a menu. The dietary information identifier may be configured to identify the at least one of the dish or the menu from the image and provide meal dietary information based on the identified at least one of the dish or the menu. The dietary management unit may be configured to store personal dietary information and to determine combined dietary information based on the personal dietary information and the meal dietary information. The image display unit may be configured to process the captured image to display the processed imaged based on the combined dietary information.

In some examples, methods to control food intake are described. Example methods may include capturing, by an image sensor, an image of at least one of a dish or a menu. Meal dietary information may be generated based on the at least one of the dish or the menu in the captured image. Based on the generated meal dietary information, combined dietary information may be generated based on the meal dietary information and personal dietary information related to previous meals. The captured image may be processed, by an image display unit, to display the processed imaged based on the combined personal dietary information.

In some examples, a computer-readable storage medium is described that may be adapted to store a program operable by a food intake controlling device. The food intake controlling device may include various features as further described herein. The program may include one or more instructions to: capture, by an image sensor, an image of at least one of a dish or a menu; generate meal dietary information based on the at least one of the dish or the menu in the captured image; determine, based on the generated meal dietary information, combined dietary information based on the meal dietary information and personal dietary information related to previous meals; and process, by an image display unit, the captured image to display the processed imaged based on the combined personal dietary information.

In some examples, food intake controlling systems are described. The food intake controlling systems may include one or more client devices coupled to a server through a communication network. Each of the one or more client devices may include one or more of an image sensor, a dietary information identifier, a dietary management unit, and/or an image display unit. The image sensor may be configured to capture an image of at least one of a dish or a menu. The dietary information identifier may be configured to identify the at least one of the dish or the menu from the image, transmit the identified at least one of the dish or the menu to the server, and receive meal dietary information from the server. The dietary management unit may be configured to store personal dietary information and to determine combined dietary information based on the meal dietary information and the personal dietary information. The image display unit may be configured to process the captured image to display the processed imaged based on the combined dietary information.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices and computer program products related to controlling food intake.

Briefly stated, technologies are generally described for controlling food intake by identifying meal dietary information based on an image of a dish or a menu and displaying the image processed based on the meal dietary information. Example devices/systems described herein may include a food intake controlling device, such as smartglasses, a tablet computer or smartphone. The food intake controlling device may include one or more of an image sensor, a dietary information identifier, a dietary management unit, and/or an image display unit. The image sensor may be configured to capture an image of a dish or a menu. The dietary information identifier may be configured to identify the dish or menu from the image. In some embodiments, identification of the dish or menu may be performed based on a user's movement that may be detected by an accelerometer or pedometer, and/or a location of the device that may be detected by a GPS sensor. In some other embodiments, identification of the dish or the menu may be performed based color or text information of the captured image. The meal dietary information may be provided based on the identified dish or the menu by the dietary information identifier or by a server (e.g., external cloud server) coupled to the dietary information identifier. The dietary management unit may be configured to store personal dietary information and to determine combined dietary information based on the personal dietary information and the meal dietary information. The image display unit may be configured to process the captured image based on the combined dietary information. For example, the image may be processed in such a manner that a part of the captured image is hidden on an image display unit or part of color or text information of the captured image is changed on the image display unit.

Figure 1:
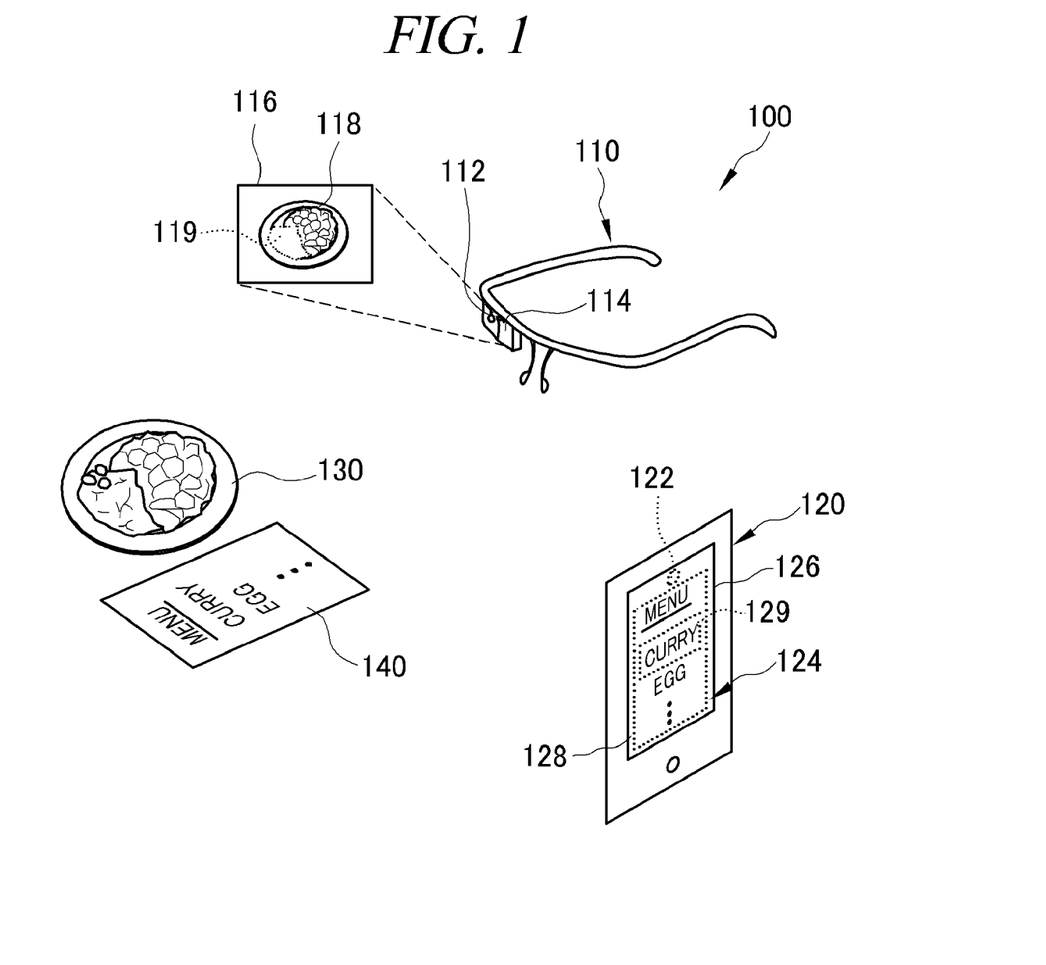
FIG. 1 illustrates a diagram of example food intake controlling devices each configured to capture an image of a dish or a menu and provide meal dietary information identified based on the captured image.

FIG. 1 illustrates a diagram of example food intake controlling devices each configured to capture an image of a dish or a menu and provide meal dietary information identified based on the captured image, arranged in accordance with at least some embodiments described herein. As depicted, FIG. 1 illustrates a scenario 100 where a user may utilize a food intake controlling device 110 such as smartglasses or a food intake controlling device 120 such as a tablet computer, each of which may be configured to capture an image of a dish 130 or a menu 140 and process the captured image. The processed image may be viewed by the user and effectively motivate the user to control food intake under dietary restrictions in such a manner as discussed below in detail.

In some embodiments, when a user who is under dietary restrictions due to diabetes, metabolic syndrome, etc. eats out at a restaurant, he/she may want to control food intake according to any calorie or nutrition allowance values. Such allowance values may be calculated based on the user's personal dietary information such as his/her dietary log as well as food intake limit prescribed by a doctor. For this purpose, the user may put on a wearable computer such as smartglasses 110 equipped with an image sensor 112 and an image display unit 114. Alternatively, the user may use a portable computer such as tablet computer 120 equipped with an image sensor 122 and an image display unit 124.

In operation, image sensor 112 of smartglasses 110 may capture an image 116 of dish 130. Based on captured image 116, smartglasses 110 may identify a dish 118 and generate meal dietary information such as a meal calorie value predetermined for identified dish 118. In some embodiments, smartglasses 110 may be further configured to detect an activity signal (e.g., the user's arm or head movement, a change in the location of smartglasses 110, etc.) by using an activity sensor (e.g., pedometer, accelerometer, GPS (global positioning system) sensor, etc.). In this case, based on the detected activity signal and/or captured image 116, smartglasses 110 may identify a dish 118 and generate meal dietary information. Alternatively or additionally, smartglasses 110 may utilize color or text information of captured image 116 to identify dish 118. Further, smartglasses 110 may determine combined dietary information based on the user's personal dietary information (e.g., the user's previously consumed calories) and the meal dietary information. Image display unit 114 of smartglasses 110 may be configured to process image 116 based on the combined dietary information and display the processed image for the user.

In some embodiments, image display unit 114 of smartglasses 110 may process image 116 in response to determining whether a dietary parameter (e.g., calorie value) of the combined dietary information exceeds a parameter allowance value (e.g., the user's personal calorie allowance value). For example, if the dietary parameter of the combined dietary information does not exceed the parameter allowance value, an image of the entire dish 118 may be processed to be visible on image display unit 114. On the other hand, if the dietary parameter of the combined dietary information exceeds the parameter allowance value, at least a part 119 of captured image 116 may be processed to be invisible or hidden on image display unit 114. In some other examples, if the dietary parameter of the combined dietary information exceeds the parameter allowance value, at least a part 119 of captured image 116 may be processed to change its color or text information on image display unit 114. In this manner, the user may be effectively motivated to control food intake and/or consume the calorie through exercise.

Similarly to smartglasses 110, image sensor 122 of tablet computer 120 may capture an image 126 of menu 140. Based on captured image 126, tablet computer 120 may identify a menu 128 and generate meal dietary information such as a meal calorie value predetermined for identified menu 128. In some embodiments, tablet computer 120 may be further configured to detect an activity signal (e.g., the user's arm or head movement, a change in the location of tablet computer 120, etc.) by using an activity sensor (e.g., pedometer, accelerometer, GPS sensor, etc.). In this case, based on the detected activity signal and/or captured image 126, tablet computer 120 may identify a menu 128 and generate meal dietary information. Alternatively or additionally, tablet computer 120 may utilize color or text information of captured image 126 to identify menu 128. Further, tablet computer 120 may determine combined dietary information based on the user's personal dietary information (e.g., the user's previously consumed calories) and the meal dietary information. Image display unit 124 of tablet computer 120 may be configured to process image 126 based on the combined dietary information and display the processed image for the user.

In some embodiments, image display unit 124 of tablet computer 120 may process image 126 in response to determining whether a dietary parameter (e.g., calorie value) of the combined dietary information exceeds a parameter allowance value (e.g., the user's personal calorie allowance value). For example, if the dietary parameter of the combined dietary information does not exceed the parameter allowance value, an image of the entire menu 128 may be processed to be visible on image display unit 124. On the other hand, if the dietary parameter of the combined dietary information exceeds the parameter allowance value, at least a part 129 of captured image 126 (e.g., a particular menu item with a high calorie value) may be processed to be invisible or hidden on image display unit 124. In some other examples, if the dietary parameter of the combined dietary information exceeds the parameter allowance value, at least a part 129 of captured image 126 may be processed to change its color or text information on image display unit 124. In this manner, the user may be effectively refrained from having food associated with the menu for which the image has been processed.

Figure 2:
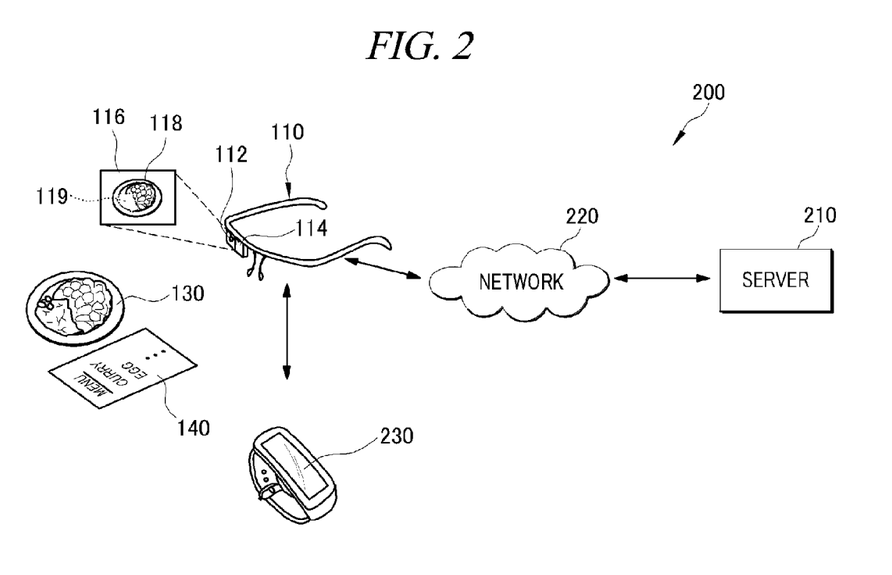
FIG. 2 illustrates a diagram of an example food intake controlling system including a client device coupled to a server through a communication network.

FIG. 2 illustrates a diagram of an example food intake controlling system including a client device coupled to a server through a communication network, arranged in accordance with at least some embodiments described herein. As illustrated, a food intake controlling system 200 may include a client device 110 coupled to a server 210 through a communication network 220. In some embodiments, client device 110 may include a configuration or function similar to food intake controlling device 110 or 120 as illustrated in FIG. 1. Further, client device 110 may be any suitable type of mobile device with wireless communication capabilities including, but not limited to, a cellular phone, a smartphone, a tablet computer, a wearable computer such as smartglasses or a smart watch, or other wireless communication device. In some embodiments, communication network 220 may be a cellular network system employing any suitable cellular technology including, but not limited to, Global System for Mobile communications (GSM), Code Division Multiple Access (CDMA), Long Term Evolution (LTE), Worldwide Interoperability for Microwave Access (WiMax) technology, and/or others.

In some embodiments, when a user who is under dietary restrictions due to diabetes, metabolic syndrome, etc., he/she may want to control food intake according to any calorie or nutrition allowance values while eating out at a restaurant or conducting any type of activity such as exercising or jogging. Such allowance values may be calculated based on the user's personal dietary information such as his/her dietary or exercise log as well as food intake limit prescribed by a doctor. For this purpose, the user may utilize client device 110 such as smartglasses equipped with an image sensor 112 and an image display unit 114. Additionally, the user may use an activity sensor 230 such as pedometer configured to detect an activity signal indicative of the user's movement.

In operation, image sensor 112 of client device 110 may capture an image 116 of dish 130. Based on captured image 116, client device 110 may identify a dish 118 and generate meal dietary information such as a meal calorie value predetermined for identified dish 118. Further, client device 110 may communicate with an activity sensor 230 such as a pedometer, which may be configured to detect an activity signal (e.g., the user's movement such as walking or jogging). In this case, client device 110 may receive the detected activity signal from activity sensor 230 and may identify a dish 118 based on the activity signal and/or captured image 116.

In some embodiments, client device 110 may transmit, to server 210, identified dish 118 and receive, from server 210, meal dietary information that is generated based on identified dish 118. Further, client device 110 may determine combined dietary information based on the user's personal dietary information (e.g., the user's previously consumed calories) and the meal dietary information. Image display unit 114 of client device 110 may process image 116 based on the combined dietary information and display the processed image for the user.

In some embodiments, image display unit 114 of client device 110 may process image 116 in response to determining whether a dietary parameter (e.g., calorie value) of the combined dietary information exceeds a parameter allowance value (e.g., the user's personal calorie allowance value). For example, if the dietary parameter of the combined dietary information does not exceed the parameter allowance value, an image of the entire dish 118 may be processed to be visible on image display unit 114. On the other hand, if the dietary parameter of the combined dietary information exceeds the parameter allowance value, at least a part 119 of captured image 116 may be processed to be invisible or hidden on image display unit 114. In some other examples, if the dietary parameter of the combined dietary information exceeds the parameter allowance value, at least a part 119 of captured image 116 may be processed to change its color or text information on image display unit 114.

Figure 3:
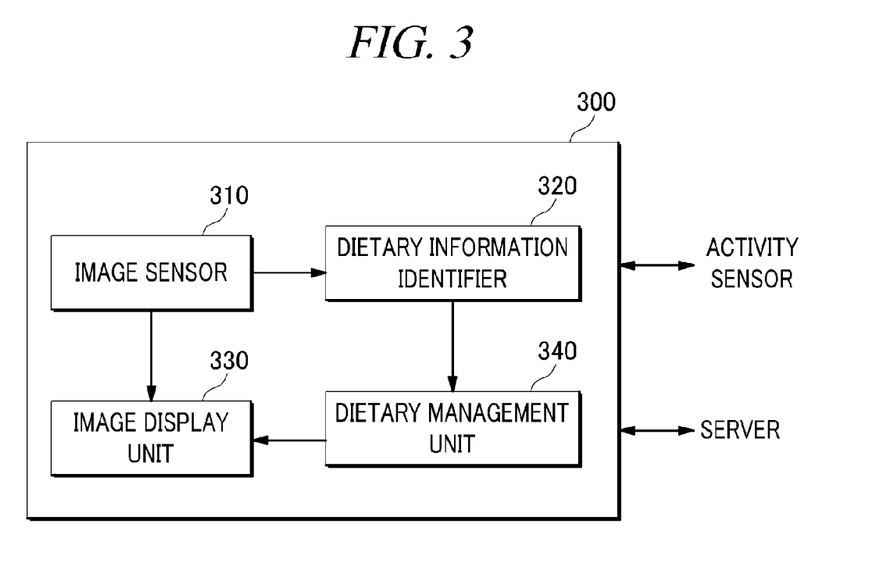
FIG. 3 illustrates a block diagram of an example food intake controlling device configured to capture an image of a dish or a menu and provide meal dietary information identified based on the captured image.

FIG. 3 illustrates a block diagram of an example food intake controlling device configured to capture an image of a dish or a menu and provide meal dietary information identified based on the captured image, arranged in accordance with at least some embodiments described herein. As depicted, a food intake controlling device 300 may include an image sensor 310, a dietary information identifier 320, an image display unit, and/or a dietary management unit 340. In some embodiments, food intake controlling device 300 may be any suitable type of mobile device with wireless communication capabilities including, but not limited to, a cellular phone, a smartphone, a tablet computer, a wearable computer such as smartglasses or smart watch, or other wireless communication device. Further, each of food intake controlling devices 110 and 120 as illustrated in FIGS. 1 and 2 may include a similar configuration as food intake controlling device 300 of FIG. 3.

In some embodiments, image sensor 310 may be configured to capture an image of at least one of a dish or a menu. Further, dietary information identifier 320 may be configured to identify the at least one of the dish or the menu from the image and provide meal dietary information based on the identified at least one of the dish or the menu. For example, the meal dietary information may include a meal calorie value.

In some embodiments, dietary information identifier 320 may be further configured to communicate with an activity sensor, which may be employed in food intake controlling device 300 or installed external to food intake controlling device 300. For example, the activity sensor may include an accelerometer configured to detect at least one of an arm movement or a head movement, a GPS sensor configured to detect a location of device 300, or a pedometer configured to detect a user's exercise or any other type of the user's activity. In case food intake controlling device 300 communicates with an accelerometer, dietary information identifier 320 may be further configured to identify the dish or the menu from the captured image based on an arm movement or head movement detected by the accelerometer. In case food intake controlling device 300 communicates with a GPS sensor, dietary information identifier 320 may be further configured to identify the dish or the menu from the captured image based on the location of device 300 detected by the GPS sensor. Additionally or alternatively, dietary information identifier 320 may be further configured to identify the dish or the menu from the captured image based on color or text information of the captured image. In some embodiments, dietary information identifier 320 may be further configured to transmit, to a server such as an external cloud server, the identified dish or menu, and receive, from the server, meal dietary information that is generated based on the identified dish or menu.

In some embodiments, dietary management unit 340 may be configured to store personal dietary information and to determine combined dietary information based on the personal dietary information and the meal dietary information. For example, the personal dietary information may include a personal calorie value. In this case, dietary management unit 340 may be further configured to determine a combined calorie value by adding the meal calorie value to the personal calorie value. Alternatively, dietary management unit 340 may be further configured to update the personal calorie value based on an activity calorie value. In some other embodiments, dietary management unit 340 may be configured to receive an activity signal from an activity sensor, and to determine an activity calorie value from the activity signal.

In some embodiments, image display unit 330 may be configured to process the captured image to display the processed imaged based on the combined dietary information. Image display unit 330 may be further configured to, when a dietary parameter of the combined dietary information exceeds a parameter allowance value, process the captured image such that at least a part of the captured image is hidden on image display unit 330. Alternatively, image display unit 330 may be further configured to, when a dietary parameter of the combined dietary information exceeds a parameter allowance value, process the captured image such that at least part of color or text information of the captured image is changed on image display unit 330. In some other embodiments, image display unit 330 may be further configured to, when the combined calorie value exceeds a personal calorie allowance value, process the captured image such that at least a hidden part of the captured image is reconstructed on image display unit 330 based on the activity calorie value.

Figure 4:
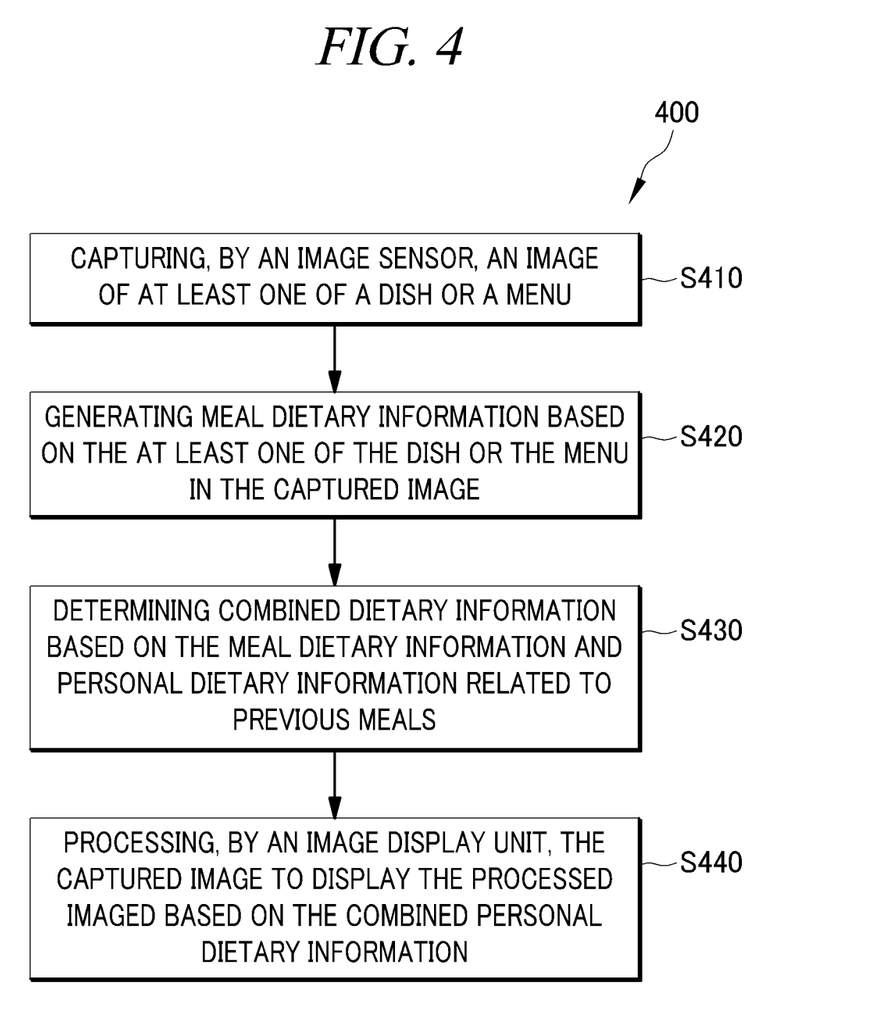
FIG. 4 illustrates an example flow diagram of a method adapted to control food intake.

FIG. 4 illustrates an example flow diagram of a method adapted to control food intake, arranged in accordance with at least some embodiments described herein. An example method 400 in FIG. 4 may be implemented using, for example, a computing device including a processor adapted to control food intake.

Method 400 may include one or more operations, actions, or functions as illustrated by one or more of blocks S410, S420, S430 and/or S440. Although illustrated as discrete blocks, various blocks may be divided into additional blocks, combined into fewer blocks, supplemented with other blocks, or eliminated, depending on the particular implementation. In some further examples, the various described blocks may be implemented as a parallel process instead of a sequential process, or as a combination thereof.

Method 400 may begin at block S410, "CAPTURING, BY AN IMAGE SENSOR, AN IMAGE OF AT LEAST ONE OF A DISH OR A MENU."

At block S410, an image of at least one of a dish or a menu may be captured by an image sensor. As depicted in FIGS. 1 to 3, image sensor 112, 122 or 310 may capture an image of at least one of a dish or a menu such as dish 130 or menu 140. Block S410 may be followed by block S420, "GENERATING MEAL DIETARY INFORMATION BASED ON THE AT LEAST ONE OF THE DISH OR THE MENU IN THE CAPTURED IMAGE."

At block S420, meal dietary information may be generated based on the at least one of the dish or the menu in the captured image. As illustrated in FIGS. 1 to 3, dietary information identifier 320 may identify the at least one of the dish or the menu from the image and provide meal dietary information based on the identified at least one of the dish or the menu. In some embodiments, dietary information identifier 320 may communicate with an activity sensor such as an accelerometer, a GPS sensor or a pedometer. In this case, dietary information identifier 320 may identify the dish or the menu from the captured image based on an arm movement or head movement detected by the accelerometer and/or the location of device 300 detected by the GPS sensor. Additionally or alternatively, dietary information identifier 320 may identify the dish or the menu from the captured image based on color or text information of the captured image. In some embodiments, dietary information identifier 320 may transmit, to a server such as an external cloud server, the identified dish or menu, and receive, from the server, meal dietary information that is generated based on the identified dish or menu. Block S420 may be followed by block S430, "DETERMINING COMBINED DIETARY INFORMATION BASED ON THE MEAL DIETARY INFORMATION AND PERSONAL DIETARY INFORMATION RELATED TO PREVIOUS MEALS."

At block S430, combined dietary information may be determined based on the meal dietary information and personal dietary information related to previous meals. As illustrated in FIGS. 1 to 3, dietary management unit 340 may determine combined dietary information based on the meal dietary information and the personal dietary information such as a personal calorie value. In some embodiments, dietary management unit 340 may determine a combined calorie value by adding the meal calorie value to the personal calorie value. In some other embodiments, dietary management unit 340 may update the personal calorie value based on an activity calorie value. In some other embodiments, dietary management unit 340 may receive an activity signal from an activity sensor, and determine an activity calorie value from the activity signal. Block S430 may be followed by block S440, "PROCESSING, BY AN IMAGE DISPLAY UNIT, THE CAPTURED IMAGE TO DISPLAY THE PROCESSED IMAGED BASED ON THE COMBINED PERSONAL DIETARY INFORMATION."

At block S440, the captured image may be processed, by an image display unit, to display the processed imaged based on the combined personal dietary information. As illustrated in FIGS. 1 to 3, image display unit 330 may process the captured image to display the processed imaged based on the combined dietary information. In some embodiments, when a dietary parameter of the combined dietary information exceeds a parameter allowance value, image display unit 330 may process the captured image such that at least a part of the captured image is hidden on image display unit 330. Alternatively, in such case, image display unit 330 may process the captured image such that at least part of color or text information of the captured image is changed on image display unit 330. In some other embodiments, when the combined calorie value exceeds a personal calorie allowance value, image display unit 330 may process the captured image such that at least a hidden part of the captured image is reconstructed on image display unit 330 based on the activity calorie value.

In light of the present disclosure, for this and other methods disclosed herein, the functions and operations performed in the methods may be implemented in differing order. Furthermore, the outlined operations are only provided as examples, and some of the operations may be optional, combined into fewer operations, supplemented with other operations, or expanded into additional operations without detracting from the essence of the disclosed embodiments.

Figure 5:
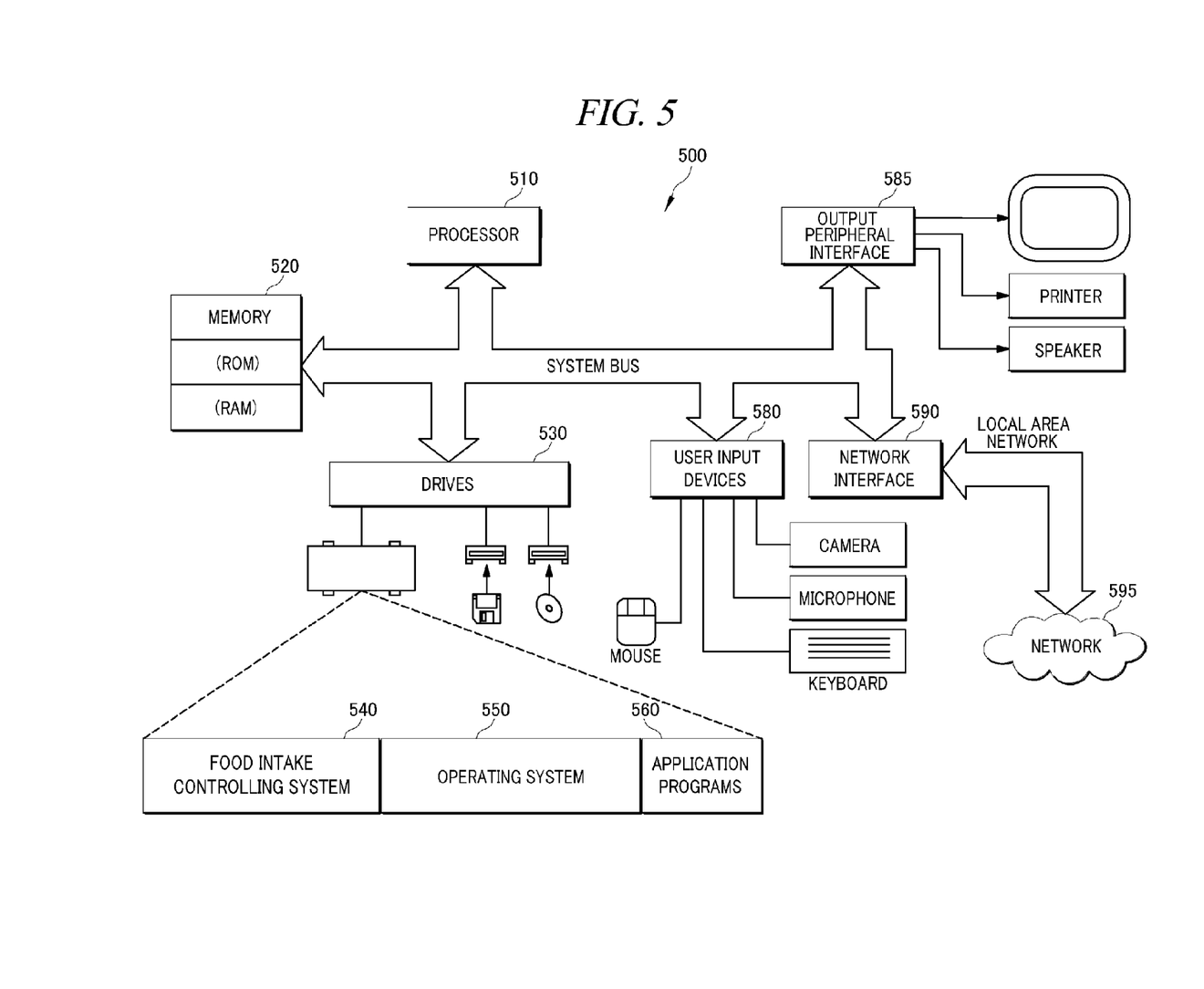
FIG. 5 shows a block diagram illustrating an example computing system that may be configured to control food intake.

FIG. 5 shows a block diagram illustrating an example computing system that may be configured to control food intake, arranged in accordance with at least some embodiments described herein. As depicted in FIG. 5, a computer 500 may include a processor 510, a memory 520 and one or more drives 530. Computer 500 may be implemented as a computer system, an embedded control computer, a laptop, or a server computer, a mobile device, a set-top box, a kiosk, a vehicular information system, a mobile telephone, a customized machine, or other hardware platform.

Drives 530 and their associated computer storage media may provide storage of computer readable instructions, data structures, program modules and other data for computer 500. Drives 530 may include a fool intake controlling system 540, an operating system (OS) 550, and application programs 560. Food intake controlling system 540 may be adapted to control food intake in such a manner as described above with respect to FIGS. 1 to 4.

Computer 500 may further include user input devices 580 through which a user may enter commands and data. Input devices may include an electronic digitizer, a camera, a microphone, a keyboard and pointing device, commonly referred to as a mouse, trackball or touch pad. Other input devices may include a joystick, game pad, satellite dish, scanner, or the like.

These and other input devices may be coupled to processor 510 through a user input interface that is coupled to a system bus, but may be coupled by other interface and bus structures, such as a parallel port, game port or a universal serial bus (USB). Computers such as computer 500 may also include other peripheral output devices such as display devices, which may be coupled through an output peripheral interface 585 or the like.

Computer 500 may operate in a networked environment using logical connections to one or more computers, such as a remote computer coupled to a network interface 590. The remote computer may be a personal computer, a server, a router, a network PC, a peer device or other common network node, and may include many or all of the elements described above relative to computer 500.

Networking environments are commonplace in offices, enterprise-wide area networks (WAN), local area networks (LAN), intranets, and the Internet. When used in a LAN or WLAN networking environment, computer 500 may be coupled to the LAN through network interface 590 or an adapter. When used in a WAN networking environment, computer 500 typically includes a modem or other means for establishing communications over the WAN, such as the Internet or a network 595. The WAN may include the Internet, the illustrated network 595, various other networks, or any combination thereof. It will be appreciated that other mechanisms of establishing a communications link, ring, mesh, bus, cloud, or network between the computers may be used.

In some embodiments, computer 500 may be coupled to a networking environment. Computer 500 may include one or more instances of a physical computer-readable storage medium or media associated with drives 530 or other storage devices. The system bus may enable processor 510 to read code and/or data to/from the computer-readable storage media. The media may represent an apparatus in the form of storage elements that are implemented using any suitable technology, including but not limited to semiconductors, magnetic materials, optical media, electrical storage, electrochemical storage, or any other such storage technology. The media may represent components associated with memory 520, whether characterized as RAM, ROM, flash, or other types of volatile or nonvolatile memory technology. The media may also represent secondary storage, whether implemented as storage drives 530 or otherwise. Hard drive implementations may be characterized as solid state, or may include rotating media storing magnetically encoded information.

Processor 510 may be constructed from any number of transistors or other circuit elements, which may individually or collectively assume any number of states. More specifically, processor 510 may operate as a state machine or finite-state machine. Such a machine may be transformed to a second machine, or specific machine by loading executable instructions. These computer-executable instructions may transform processor 510 by specifying how processor 510 transitions between states, thereby transforming the transistors or other circuit elements constituting processor 510 from a first machine to a second machine. The states of either machine may also be transformed by receiving input from user input devices 580, network interface 590, other peripherals, other interfaces, or one or more users or other actors. Either machine may also transform states, or various physical characteristics of various output devices such as printers, speakers, video displays, or otherwise.

Figure 6:
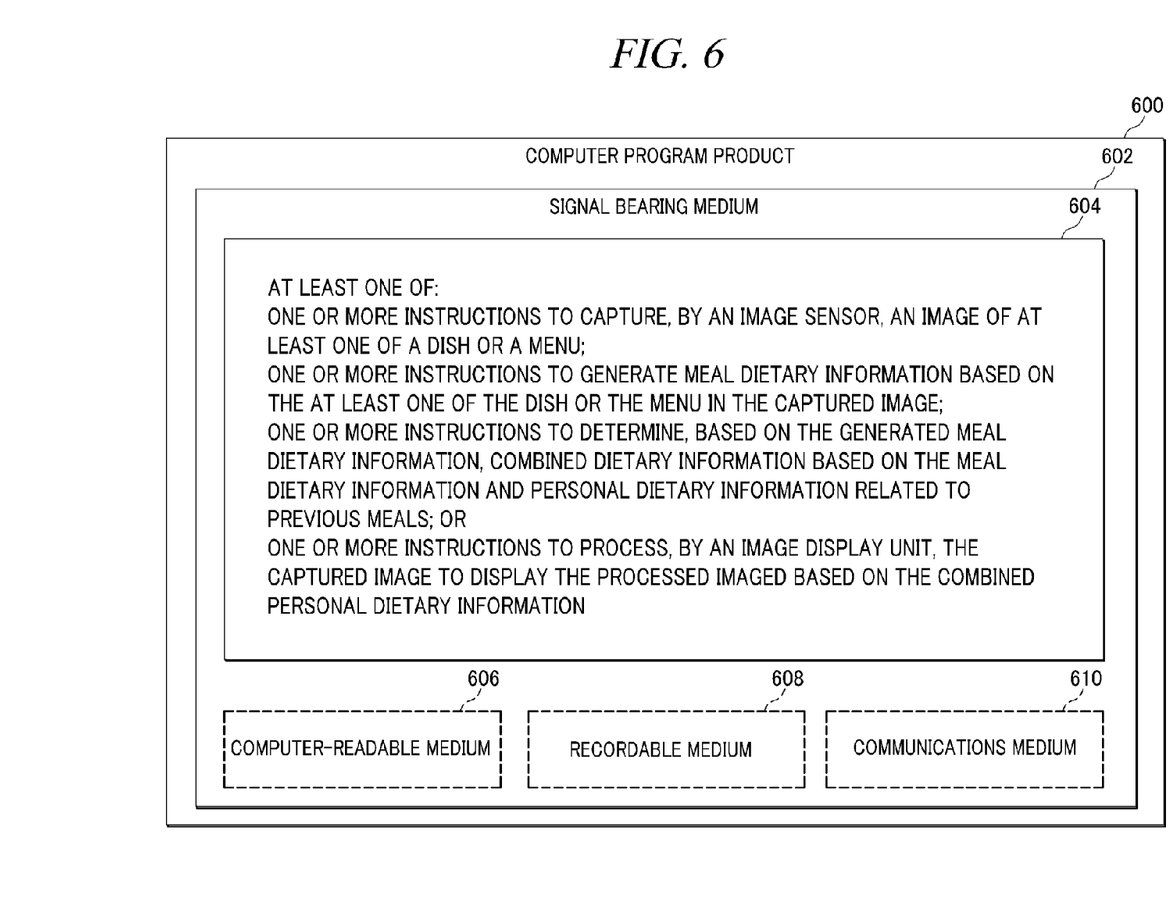
FIG. 6 illustrates a computer program product that may be utilized to control food intake, all arranged in accordance with at least some embodiments described herein.

FIG. 6 illustrates a computer program product that may be utilized to control food intake, in accordance with at least some embodiments described herein. Program product 600 may include a signal bearing medium 602. Signal bearing medium 602 may include one or more instructions 604 that, in response to execution by, for example, a processor, may provide the functionality and features described above with respect to FIGS. 1 to 5. By way of example, instructions 604 may include at least one of: one or more instructions to capture, by an image sensor, an image of at least one of a dish or a menu; one or more instructions to generate meal dietary information based on the at least one of the dish or the menu in the captured image; one or more instructions to determine, based on the generated meal dietary information, combined dietary information based on the meal dietary information and personal dietary information related to previous meals; or one or more instructions to process, by an image display unit, the captured image to display the processed imaged based on the combined personal dietary information. Thus, for example, referring to FIGS. 1 to 3, food intake controlling device 110, 120 or 300 may undertake one or more of the blocks shown in FIG. 4 in response to instructions 604.

In some implementations, signal bearing medium 602 may encompass a non-transitory computer-readable medium 606, such as, but not limited to, a hard disk drive, a Compact Disc (CD), a Digital Video Disk (DVD), a digital tape, memory, etc. In some implementations, signal bearing medium 602 may encompass a recordable medium 608, such as, but not limited to, memory, read/write (R/W) CDs, R/W DVDs, etc. In some implementations, signal bearing medium 602 may encompass a communications medium 610, such as, but not limited to, a digital and/or an analog communication medium (e.g., a fiber optic cable, a waveguide, a wired communications link, a wireless communication link, etc.). Thus, for example, program product 600 may be conveyed to one or more modules of food intake controlling device 110, 120 or 300 by an RF signal bearing medium 602, where the signal bearing medium 602 is conveyed by a wireless communications medium 610 (e.g., a wireless communications medium conforming with the IEEE 802.11 standard).

In some embodiments, a food intake controlling device comprises: an image sensor configured to capture an image of at least one of a dish or a menu; a dietary information identifier configured to identify the at least one of the dish or the menu from the image and provide meal dietary information based on the identified at least one of the dish or the menu; a dietary management unit configured to store personal dietary information and to determine combined dietary information based on the personal dietary information and the meal dietary information; and an image display unit configured to process the captured image to display the processed imaged based on the combined dietary information. In some embodiments, a user may be under dietary restrictions for medical, lifestyle, personal improvement, or personal preference reasons. In some examples, a user may be under dietary restrictions due to diabetes, metabolic syndrome, and the like, or may desire to restrict intake of calories and/or other dietary component(s). The processed image may be modified to only show food options that conform to one or more predetermined dietary restrictions. For example, a processed image may only show menu information restricted to options that comply with a dietary restriction, for example in view of records kept in relation to the user in a dietary log, and the like.

In some embodiments, only dishes whose calories do not exceed a permitted calorie intake are made visible in the processed image (e.g. menu information modified based on dietary restrictions and/or other data relating to the user, such as exercise data), for example at an eating or drinking establishment. Dishes (or other food and drink options) with a calorie content exceeding a permitted (for example) calorie intake (or other dietary restriction) may be made invisible (e.g. removed from a displayed processed image), less visible, or in some examples made to appear unattractive in the processed image containing modified menu information. In some embodiments, modified menu information may be displayed as a processed image displayed on a screen of a portable electronic device, such as a smartphone, and the like, head-up display, and the like. A processed image may include text modified from original text menu information, or may selectively exclude such information. In some embodiments, menu options may be made invisible when, for example, the calorie or other dietary content of a dish exceeds a permitted intake.

In some embodiments, the motivation of a user under dietary restrictions may be increased by partially obscuring menu options, for example using image processing such as shading, partially obscuring, low contrast (e.g. low contrast colors), low brightness, partial transparency, and the like, display of information. For example, as a user's calorie intake approaches a predetermined limit, for example approaching a level at which a certain dish becomes prohibited for the user, the display of the corresponding menu may be displayed gradually fainter so that the user will consider stopping or reducing further food intake, or may be motivated to exercise or otherwise expend calories. In some examples, if the permitted calorie intake approaches a level at which a certain dish becomes permitted for the user as a result of calorie consumption through exercise, the display of the corresponding menu may become gradually more visible, for example increasing in intensity and/or contrast. In some embodiments, encouraging messages may be sent to the user, for example "Try exercising."

In some embodiments, image processing may be used to modify a menu display so that a user under dietary restrictions due to diabetes, metabolic syndrome, and the like, is made aware whether or not a food (or drink) selection complies with a permitted intake (of calories and/or other dietary component).

In some embodiments, image processing may include modifying an image of the food option to make it seem less appealing, for example using unpleasant color shades (such as green, brown, grey, and the like, which may be selected to conflict with the expected color of a food item), addition of unpleasant images (such as insects, vermin, and the like) superimposed on, or adjacent to, a food image (where unpleasant images may be selected to induce feelings of disgust in the user), displaying images of a projected appearance of the user if they continue to select such food options, and the like. Image processing may include modification of the appearance of text information displayed to the user.

In some embodiments, dietary restrictions may comprise one or more dietary restrictions selected from total calorie intake, net calorie intake (after adjustment for calories expended by exercise and the like), fat content, carbohydrate intake (such as sugar intake), alcohol intake, protein intake (for which there may be a predetermined minimum intake which a user prefers to exceed), salt, and one or more food additives (such as monosodium glutamate, flavoring chemicals, coloring chemicals, preservatives, and the like). In some cases, fluid intake may be monitored, and if insufficient a user may be guided to imbibe more fluid. Alcohol intake may be monitored, and drink options presented to a person may be restricted to low or zero alcohol options after a predetermined total alcohol intake, or estimated or measured blood alcohol content, is reached.

In some embodiments, a device, such as an augmented reality viewer, is configured so that when a restaurant menu is viewed, menu items that fail to comply with dietary restrictions are filtered from view, or otherwise made invisible or difficult for a user to see. A time-dependent dietary allowance may be calculated based upon e.g. what the user has eaten and what exercise the user has performed. In some examples, an augmented reality may be viewed through one or more displays, for example through suitably configured smart glasses. In some examples, a person may view a display of a portable electronic device, and modified menu information may be displayed on the display. In some examples, an electronic menu display associated with a restaurant may communicate with a portable electronic device associated with a user, and selectively display options that conform to dietary restrictions, preferences, and the like.

The present disclosure is not to be limited in terms of the particular embodiments described in this application, which are intended as illustrations of various aspects. Many modifications and variations may be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure includes the terms of the appended claims, along with the full scope of equivalents to which such claims are entitled. This disclosure is not limited to particular methods, reagents, compounds, compositions or biological systems, which can, of course, vary. The terminology used herein is for the purpose of describing particular embodiments only, and is not intended to be limiting.

The herein described subject matter sometimes illustrates different components contained within, or connected with, different other components. Such depicted architectures are merely examples, and in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, various embodiments of the present disclosure have been described herein for purposes of illustration, and various modifications may be made without departing from the scope and spirit of the present disclosure. Accordingly, the various embodiments disclosed herein are not intended to be limiting, with the true scope and spirit being indicated by the following claims.

What is claimed is:

1. A food intake controlling device comprising:
   an image sensor configured to capture a captured image of at least one of a dish or a menu;
   a global positioning system (GPS) sensor configured to detect a location of the food intake controlling device;
   a dietary information identifier configured to:
      identify the at least one of the dish or the menu from the captured image based on the location of the food intake controlling device, and
      provide meal dietary information based on the identified at least one of the dish or the menu,
      wherein the meal dietary information includes a meal calorie value;
   a dietary management unit configured to store personal dietary information, wherein the personal dietary information includes a previously consumed calorie value and to determine combined dietary information based on the personal dietary information and the meal dietary information,
    wherein the dietary management unit is further configured to determine a combined calorie value of the combined dietary information by adding the meal calorie value to the previously consumed calorie value; and
an image display unit configured to:
    determine whether the combined calorie value of the combined dietary information exceeds a parameter allowance value,
    process the captured image to display a processed image based on the combined calorie value by processing the captured image such that at least a part of the captured image becomes less visible on the image display unit based on a determination that the combined calorie value exceeds the parameter allowance value, and
    project an augmented future physical appearance of a user when the user continues to consume the dish from the less visible part of the processed image.

2. The device of claim 1, further comprising an accelerometer configured to detect at least one of an arm movement or a head movement,
    wherein the dietary information identifier is further configured to identify the at least one of the dish or the menu from the captured image based on the detected at least one of the arm movement or the head movement.

3. The device of claim 1, wherein the dietary information identifier is further configured to identify the at least one of the dish or the menu from the captured image based on color or text information of the captured image.

4. The device of claim 1, wherein the image display unit is further configured to, when the combined calorie value of the combined dietary information exceeds the parameter allowance value, process the captured image such that at least the part of the captured image is hidden on the image display unit.

5. The device of claim 1, wherein the image display unit is further configured to, when the combined calorie value of the combined dietary information exceeds the parameter allowance value, process the captured image such that at least part of color or text information of the captured image is changed on the image display unit.

6. The device of claim 1,
    wherein the dietary management unit is further configured to update the previously consumed calorie value based on an activity calorie value.

7. The device of claim 6, wherein the dietary management unit is configured to receive an activity signal from an activity sensor, and to determine the activity calorie value from the activity signal.

8. The device of claim 6, wherein the image display unit is further configured to, when the combined calorie value of the combined dietary information exceeds the parameter allowance value, process the captured image such that at least a hidden part of the captured image is reconstructed on the image display unit based on the activity calorie value.

9. The device of claim 1, wherein the device is at least one of smartglasses, a tablet computer, or a smartphone.

10. The device of claim 1, wherein the dietary information identifier is further configured to transmit, to an external cloud server, the identified at least one of the dish or the menu; and receive, from the external cloud server, the meal dietary information that is generated based on the identified at least one of the dish or the menu.

11. A method to control food intake under control of a device, the method comprising:
    capturing, by an image sensor, a captured image of at least one of a dish or a menu;
    detecting, by a global positioning system (GPS) sensor, a location of the device;
    identifying the at least one of the dish or the menu from the captured image based on the detected location of the device;
    generating meal dietary information based on the identified at least one of the dish or the menu in the captured image;
    determining, combined dietary information based on the meal dietary information and personal dietary information related to previous meals,
        wherein the meal dietary information includes a meal calorie value and the personal dietary information includes a previously consumed calorie value, and
        wherein the determination of the combined dietary information comprises determining a combined calorie value by adding the previously consumed calorie value to the meal calorie value;
    determining whether the combined calorie value of the combined dietary information exceeds a parameter allowance value; and
    processing, by an image display unit, the captured image to display a processed image based on the combined calorie value such that at least a part of the captured image becomes less visible on the image display unit based on the determination that the combined calorie value exceeds the parameter allowance value, and
    projecting, by the image display unit, an augmented future physical appearance of a user when the user continues to consume the dish from the less visible part of the processed image.

12. The method of claim 11, further comprising:
    detecting, by an accelerometer, at least one of an arm movement or a head movement, wherein identifying the at least one of the dish or the menu comprises identifying the at least one of the dish or the menu from the captured image based on the detected at least one of the arm movement or the head movement.

13. The method of claim 11, wherein identifying the at least one of the dish or the menu comprises identifying the at least one of the dish or the menu from the captured image based on color or text information of the captured image.

14. The method of claim 11, wherein processing the image comprises, when the combined calorie value of the combined dietary information exceeds the parameter allowance value, processing the captured image by the image display unit such that at least the part of the captured image is hidden on the image display unit.

15. The method of claim 11, wherein processing the image comprises, when the combined calorie value of the combined dietary information exceeds the parameter allowance value, processing the captured image by the image display unit such that at least part of color or text of the captured image is changed on the image display unit.

16. The method of claim 11, further comprising:
    updating the personal calorie value based on an activity calorie value that is determined based on an activity signal received from an activity sensor.

17. The method of claim 16, wherein processing the image comprises, when the combined calorie value of the combined dietary information exceeds the parameter allowance value, further processing the captured image by the image display unit such that at least a hidden part of the captured image is reconstructed on the image display unit based on the activity calorie value.

18. The method of claim 11, further comprising:
transmitting the at least one of the dish or the menu to an external cloud server; and
receiving, from the external cloud server, the meal dietary information that is generated based on the at least one of the dish or the menu.

\* \* \* \* \*

UNITED STATES PATENT AND TRADEMARK OFFICE
CERTIFICATE OF CORRECTION

PATENT NO. : 9,881,518 B2
APPLICATION NO. : 14/547703
DATED : January 30, 2018
INVENTOR(S) : Kuwahara et al.

It is certified that error appears in the above-identified patent and that said Letters Patent is hereby corrected as shown below:

In the Specification

In Column 6, Line 64, delete "device 300," and insert -- food intake controlling device 300, --, therefor.

In Column 7, Line 7, delete "device 300" and insert -- food intake controlling device 300 --, therefor.

In Column 8, Line 24, delete "device 300" and insert -- food intake controlling device 300 --, therefor.

In Column 10, Line 1, delete "communications link," and insert -- communication link, --, therefor.

In Column 10, Line 42, delete "Program product 600" and insert -- Computer program product 600 --, therefor.

In Column 10, Line 65, delete "hard disk drive," and insert -- hard disk drive (HDD), --, therefor.

In Column 11, Line 7, delete "communications link," and insert -- communication link, --, therefor.

In Column 11, Line 8, delete "program product 600" and insert -- computer program product 600 --, therefor.

In Column 13, Line 48, delete "recitation no" and insert -- recitation, no --, therefor.

In Column 14, Line 3, delete "general such" and insert -- general, such --, therefor.

In Column 14, Line 10, delete "general such" and insert -- general, such --, therefor.

Signed and Sealed this
Twenty-second Day of May, 2018

Andrei Iancu
*Director of the United States Patent and Trademark Office*